(12) United States Patent
Dewis et al.

(10) Patent No.: US 8,075,937 B2
(45) Date of Patent: *Dec. 13, 2011

(54) ALKYLDIENAMIDES EXHIBITING TASTE AND SENSORY EFFECT IN FLAVOR COMPOSITIONS

(75) Inventors: Mark L. Dewis, Matawan, NJ (US); Michelle E. Huber, Chadds Ford, PA (US); Michael V. Cossette, Plainsboro, NJ (US); David O. Agyemang, Sayreville, NJ (US); Garry Conklin, Pequannock, NJ (US); Tao Pei, Morganville, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 131 days.

This patent is subject to a terminal disclaimer.

(21) Appl. No.: 12/544,822

(22) Filed: Aug. 20, 2009

(65) Prior Publication Data
US 2009/0311402 A1     Dec. 17, 2009

Related U.S. Application Data

(60) Division of application No. 10/783,652, filed on Feb. 20, 2004, now Pat. No. 7,632,531, which is a continuation-in-part of application No. 10/411,672, filed on Apr. 11, 2003, now Pat. No. 7,361,376.

(51) Int. Cl.
*A23L 1/22*     (2006.01)

(52) U.S. Cl. .......... 426/534; 426/590; 426/650; 554/35; 554/69

(58) Field of Classification Search ............... 426/534, 426/536, 537, 538, 590, 650; 554/35, 69
See application file for complete search history.

(56) References Cited

U.S. PATENT DOCUMENTS 7,361,376 B2 *    4/2008    Dewis et al. ............... 426/534

* cited by examiner

*Primary Examiner* — Leslie Wong
(74) *Attorney, Agent, or Firm* — Elizabeth M. Quirk; XuFan Tseng; Joseph F. Leightner

(57) ABSTRACT

Alkyldienamides compounds suitable for use as flavoring agents are disclosed. The compounds are used as flavors since they possess umami characteristics or other desirable organoleptic properties. The disclosed compounds are defined by the structure set forth below:

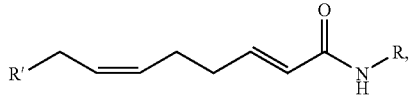

wherein R is ethyl or cyclopropyl; and
wherein R' is methyl or butyl,
with the proviso that when R is ethyl, R' is not methyl.

6 Claims, No Drawings

ALKYLDIENAMIDES EXHIBITING TASTE AND SENSORY EFFECT IN FLAVOR COMPOSITIONS

STATUS OF RELATED APPLICATIONS

This application is a divisional of U.S. Ser. No. 10/783,652, filed Feb. 20, 2004, now U.S. Pat. No. 7,632,531, which is a continuation-in-part of U.S. Ser. No. 10/411,672, filed Apr. 11, 2003, now U.S. Pat. No. 7,361,376, each of which is hereby incorporated by reference in its entirety.

FIELD OF THE INVENTION

Alkamide compounds having umami taste and somatosensory attributes in the oral cavity.

BACKGROUND OF THE INVENTION

The term Umami, from the Japanese word to describe savory or meaty, is the term used to describe the unique overall fullness, savory or salivatory taste of food. Materials that exhibit this taste quality generally potentiate the intensity of glutamate solutions and this is one important characteristic of umami taste. It is increasingly becoming recognized as the fifth sense of taste, the others being sour, sweet, salt and bitter. Compounds traditionally described as possessing this character are monosodium glutamate (MSG), protein hydrolysates, some amino acids and certain nucleotides and phosphates.

MSG is the most widely used material as a "taste enhancer" where it synergizes the perception of "savory" ingredients, but has also been alleged to cause allergic reaction to a proportion of the population. Since MSG is widely used in Asian cuisine, especially Chinese, this has been referred to as the Chinese Restaurant Syndrome. Free glutamic acid occurs in food but this also is the subject of review by The Federation of American Society for Experimental Biology.

Among other chemical compounds several nucleotides have also been described to exhibit the umami effect Adenosine 5'-(trihydrogen diphosphate), 5'-Cytidylic acid (5'-CMP), 5'-Uridylic acid (5'-UMP), 5'-Adenylic acid (5'-AMP), 5'-Guanylic acid (5'-GMP), 5'-Inosinic acid (5'-IMP) and the di-sodium salts of 5'-Guanylic acid and 5'-Inosinic acid.

Recent literature cites an extensive range of other organic compounds as taste active components of mixtures shown to give the umami taste effect. These include but are not necessarily limited to: organic acids such as succinic acid, lactic acid, saturated straight chain aliphatic acids of six, eight, fourteen, fifteen, sixteen, and seventeen carbon chain lengths, Z4,Z7, Z10,Z13,Z16,Z19-docosahexaenoic acid, Z5,Z8, Z11,Z14,Z17-eicosapentaenoic acid, Z9,Z12, Z16, Z19-octadecadienoic acid, Z9-octadecenoic acid, glutaric acid, adipic acid, suberic acid, and malonic acid. Aminoacids having umami effects reported in the literature include glutamic acid, aspartic acid, threonine, alanine, valine, histidine, proline tyrosine, cystine, methionine, pyroglutamic acid, leucine, lycine, and glycine. Dipeptides possessing umami properties include Val-Glu and Glu-Asp.

Other miscellaneous compounds having umami properties include alpha-amino adipic acid, malic acid, alpha-aminobutyric acid, alpha-aminoisobutyric acid, E2,E4-hexadienal, E2,E4-heptadienal, E2,E4-octadienal, E2,E4-decadienal, Z4-heptenal, E2,Z6-nonadienal, methional, E3,E5-octadien-2-one, 1,6-hexanediamine, tetramethylpyrazine, trimethylpyrazine, cis-6-dodecen-4-olide and a number of naturally occurring amino-acids.

The discovery of alkyldienamides in a wide variety of botanicals and the use of some of these to impart flavor and/or a sensation is the subject of a huge amount of literature. Molecules of this type have also been found to exhibit biological activity, most notably anti-bacterial, anti-fungal and insecticidal activity. The most significant compounds in this class, provided with their Chemical Abstract Service number in brackets are: hydroxy-alpha-sanshool [83883-10-7], alpha-sanshool [504-97-2], hydroxy-epislon-sanshool [252193-26-3], gamma-sanshool [78886-65-4], spilanthol [25394-57-4], N-isobutyl E2,E4,8,11-dodecatetraenamide [117824-00-7 and 310461-34-8], isoaffinin [52657-13-3], pellitorine [18836-52-7] and bunganool [117568-40-8] along with a small number of geometrical isomers thereof.

Despite these disclosures there is an ongoing need for new flavor ingredients particularly those that exhibit advantageous organoleptic properties.

SUMMARY OF THE INVENTION

Our invention relates to novel compounds and a process for augmenting or imparting a taste or somatosensory effect to a foodstuff, chewing gum, medicinal product, toothpaste, alcoholic beverage, aqueous beverage or soup comprising the step of adding to a foodstuff, chewing gum, medicinal product, toothpaste, alcoholic beverage, aqueous beverage or soup a taste or sensation augmenting, enhancing or imparting quantity and concentration of at least one N-substituted unsaturated aliphatic alkyl amide defined according to the structure:

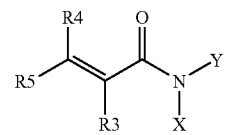

wherein X is selected from the group consisting of H, methyl, ethyl, n-propyl, and isopropyl;

Y is selected from the group consisting of methyl, ethyl, cyclopropyl, isopropyl, n-propyl, n-butyl, sec-butyl, isobutyl, 2-methylbutyl, allyl, cyclobutyl,

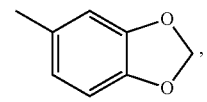

cyclobutyl, $CH_2CH(OH)CH_3$, $CH(CH_3)CH_2OH$, $CH_2C(CH_3)OH$, $CH_2CH_2OH$, $CH_2CO_2CH_3$, gernyl, and neryl;

or X and Y taken together is selected form the group consisting of the structures:

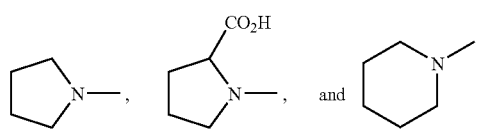

$R^3$ is selected from the group consisting of methyl and H;
$R^4$ is selected from the group consisting of methyl and H;
$R^5$ is selected from the group consisting of methyl, phenyl, benzyl, ethyl, propyl, butyl, isopropyl, phenylethyl,

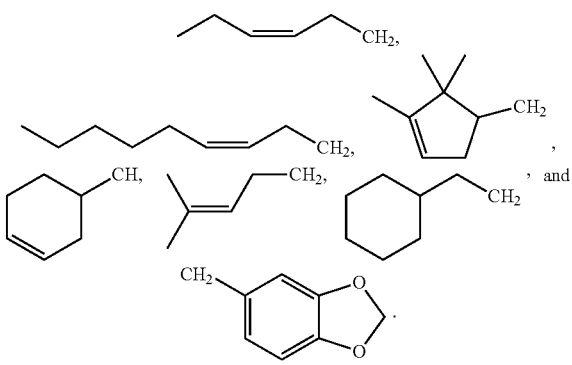
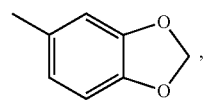

In a highly preferred embodiment of the invention, the amides have the structure set forth below:

cyclopentyl, and allyl; and
wherein R' is selected from the group consisting of methyl, ethyl, n-propyl, n-butyl, n-pentyl, and n-hexyl.

As used herein these compounds will be referred hereinafter to as "alkyldienamides."

DETAILED DESCRIPTION OF THE INVENTION

Our invention specifically relates to the novel compositions according to the formulas above, which have been described as having the following flavor characteristics:

| R | R' | Compound | Primary Characteristic | Secondary Characteristic |
|---|---|---|---|---|
| $CH_2CH_2OH$ | n-butyl | N-(2-Hydroxyethyl) E2,Z6-dodecadienamide | Tingle, melon flavor | Pepper like warmth |
| $CH_2CH(CH_3)CH_2CH_3$ | n-butyl | N-(2-Methylbutyl) E2,Z6-dodecadienamide | Fruity | Salt like |
| (3,4-methylenedioxybenzyl group) | Me | N-(3,4-Methylenedioxy)benzyl E2,Z6-nonadienamide | Numbing | Tingle |
| $CH_2CH(CH_3)CH_2CH_3$ | Me | N-(2-Methylbutyl) E2,Z6-nonadienamide | Bitter | Tingle |
| cyclopropyl | n-butyl | N-Cyclopropyl E2,Z6-dodecadienamide | Fatty mouthfeel | Wasabi type burn |
| cyclopropyl | Me | N-Cyclopropyl E2,Z6-nonadienamide | Umami | Enhancement |
| ethyl | n-butyl | N-Ethyl E2,Z6-dodecadienamide | MSG like | Burning |
| ethyl | Me | N-Ethyl E2,Z6-nonadienamide | Umami | Enhancement |
| isobutyl | n-butyl | N-Isobutyl E2,Z6-dodecadienamide | Numbing | Tingle |
| isobutyl | Me | N-Isobutyl E2,Z6-nonadienamide | Tingle/numbing | MSG like |
| isopropyl | n-butyl | N-Isopropyl E2,Z6-dodecadienamide | Melon/cucumber Flavor | Tingle |
| isopropyl | Me | N-Isopropyl E2,Z6-nonadienamide | Cucumber taste | Tingle |
| Me | Me | N-Methyl E2,Z6-nonadienamide | Tingle | Numbing |

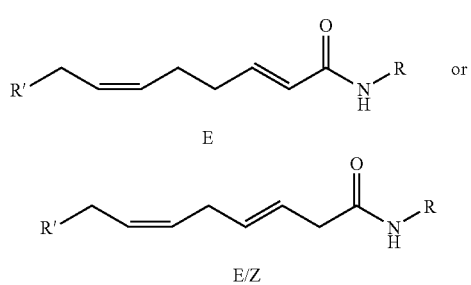

wherein R is selected from the group consisting of methyl, ethyl, n-propyl, isopropyl, cyclopropyl, n-butyl, sec-butyl, isobutyl, cyclobutyl, $CH_2CH(CH_3)CH_2CH_3$, $CH_2CH(OH)CH_3$, $CH(CH_3)CH_2OH$, $CH_2C(CH_3)_2OH$, $CH_2CH_2OH$, and uses thereof in augmenting or imparting an olfactory effect or sensation such as a taste or somatosensory effect to a foodstuff, chewing gum, medicinal product, toothpaste, alcoholic beverage, aqueous beverage or soup, particularly providing a (a) umami taste, (b) tingle sensation, (c) warming/burning sensation, (d) numbing sensation, (e) cooling sensation, and (f) salt effects.

More specifically, examples of the organoleptic properties for the alkyldienamides of our invention are as follows:

| Compound | Taste and Flavor Characteristics |
|---|---|
| N-(2-Hydroxypropyl) E2,Z6-nonadienamide | Cloying, fatty, cod liver oil, fishy. |
| N-(2-Hydroxyethyl) E2,Z6-dodecadienamide | Strong melon flavor, tingle, burn, pepper taste. |

| Compound | Taste and Flavor Characteristics |
|---|---|
| N-(2-Methylbutyl) E2,Z6-dodecadienamide | Slightly fruity, tingle, salty. |
| N-(3,4-Methylenedioxy) benzyl E2,Z6-nonadienamide | Numbing and tingle. |
| N-(2-Methylbutyl) E2,Z6-nonadienamide | Metallic, bitter, tingle. |
| N-Cyclopropyl E2,Z6-dodecadienamide | Fatty mouthfeel, tongue burn, Wasabi like |
| N-Cyclopropyl E2,Z6-nonadienamide | Oily, tingle, strong MSG/umami mouthfeel. |
| N-Ethyl E2,Z6-dodecadienamide | Burn, MSG effect, oily flavor, green celery, sweet heating. |
| N-Ethyl E2,Z6-nonadienamide | Umami character |
| N-Isobutyl E2,Z6-dodecadienamide | Some tingle, anesthetic, numbing effect, interesting cooling/tingle effect, long lasting. The aftertaste is cooling and refreshing. |
| N-Isobutyl E2,Z6-nonadienamide | Strong tingle very long lasting, mint, oily, fizzy, tongue numbing, some MSG effect. |
| N-Isopropyl E2,Z6-dodecadienamide | Oily flavor, slight tingle. |
| N-Isopropyl E2,Z6-nonadienamide | Oily, cucumber, some tingle, bitter. |
| N-Methyl E2,Z6-nonadienamide | Warming, tingle |

Other compounds of the present invention include the following:

| Name | Structure |
|---|---|
| N-Ethyl 3-(cyclohex-3-en-1-yl) E2-propenamide | |
| N-Cyclopropyl 3-(cyclohex-3-en-1-yl) E2-propenamide | 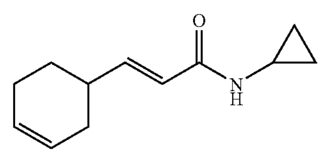 |
| N-Ethyl-4-(2,2,3-trimethylcyclopent-3-en-1-yl) E2-butenamide | 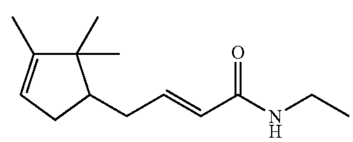 |
| N-Cyclopropyl-4-(2,2,3-trimethylcyclopent-3-en-1-yl) E2-butenamide | 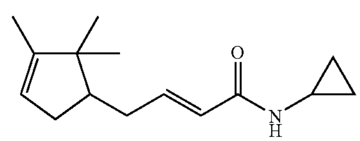 |
| N-Isopropyl E2,Z6-nonadienamide | 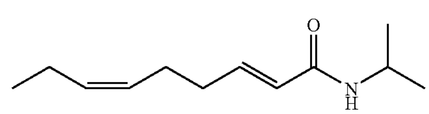 |
| N-Ethyl E2,Z6-nonadienamide | 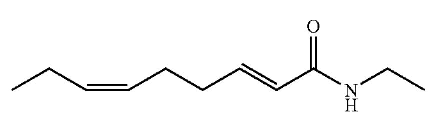 |
| N-Methyl E2,Z6-nonadienamide | 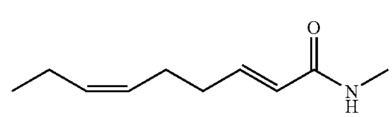 |
| N-Isobutyl E2,Z6-nonadienamide | 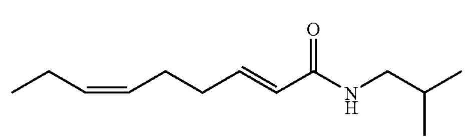 |

-continued

| Name | Structure |
|---|---|
| N-(2-Methylbutyl) E2,Z6-nonadienamide | 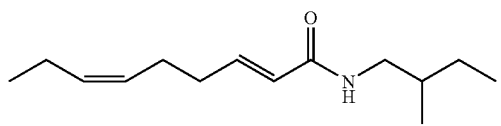 |
| N-Cyclopropyl E2,Z6-nonadienamide | 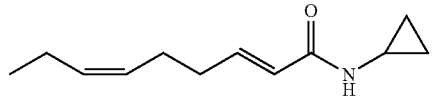 |
| N-(2-Hydroxypropyl) E2,Z6-nonadienamide | 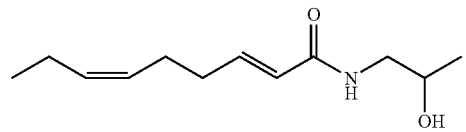 |
| N-(3,4-Methylenedioxy) benzyl E2,Z6-nonadienamide | 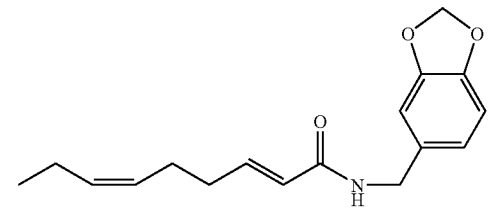 |
| N-Allyl E2,Z6-nonadienamide | 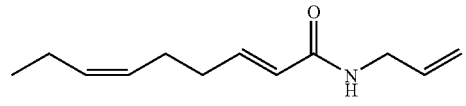 |
| N-(Carboxymethyl)methyl E2,Z6-nonadienamide | 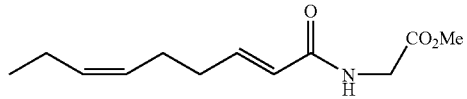 |
| N,N-Dimethyl E2,Z6-nonadienamide | 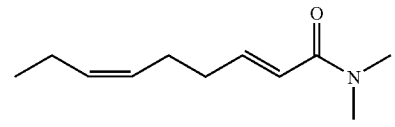 |
| N-Methyl E2,Z6-dodecadienamide | 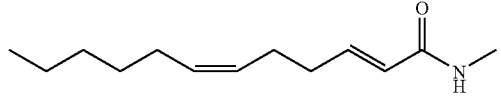 |
| N-Ethyl E2,Z6-dodecadienamide | 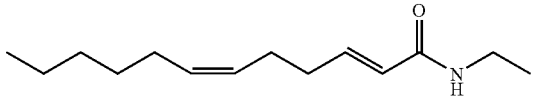 |
| N-Cyclopropyl E2,Z6-dodecadienamide | 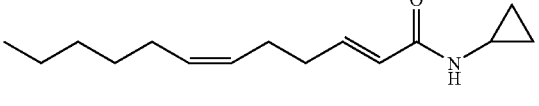 |
| N-Isopropyl E2,Z6-dodecadienamide | 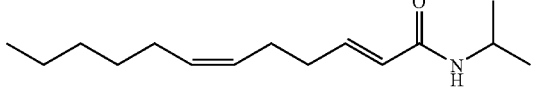 |
| N-Isobutyl E2,Z6-dodecadienamide | 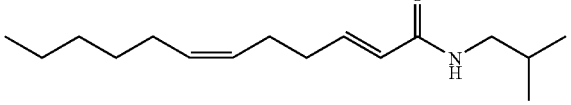 |

-continued

| Name | Structure |
|---|---|
| N-(2-Hydroxyethyl) E2,Z6-dodecadienamide | 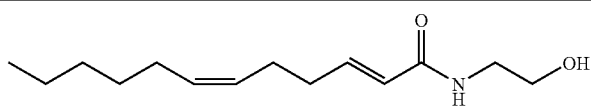 |
| N-(2-Methylbutyl) E2,Z6-dodecadienamide | 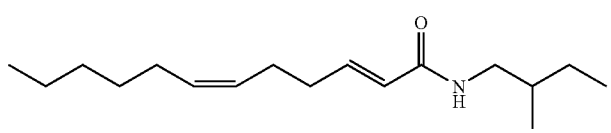 |
| N-Isobutyl 3,4-(dioxymethylene) cinnamide | 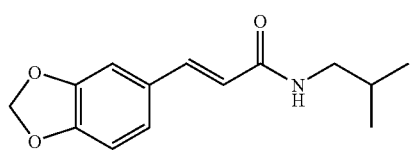 |
| Piperidyl 3,4-(dioxymethylene) cinnamide | 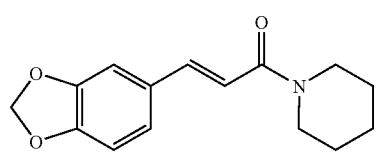 |
| N,N-Diisopropyl 3-methyl-2-hexenamide | 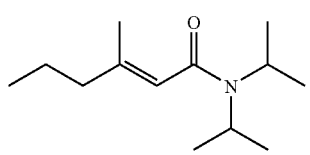 |
| N,N-Dimethyl 3,7-dimethyl-2,6-octadienamide | 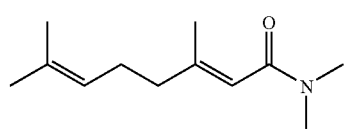 |
| N-Ethyl 5-phenyl-E2-pentenamide | 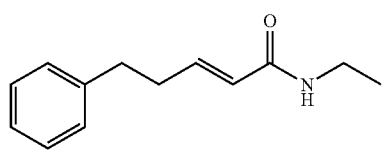 |
| N,N-Ethyl 3,7-dimethyl-2,6-octadienamide | 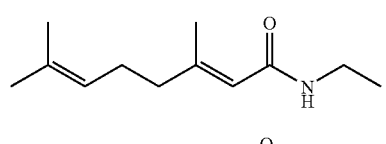 |
| N-Ethyl 5-phenyl-E2-pentenamide | 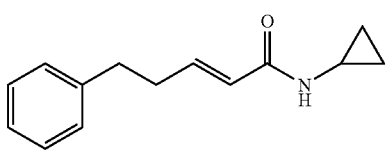 |

The literature has not previously reported alkyldienamides having umami flavor. In addition, closely structurally related compounds such as dienals and unsaturated acids, are not specifically reported to possess umami character when tasted in isolation. In addition the ability to provide an enhanced saltiness for the product without increasing sodium level is not disclosed or suggested by the prior art. The salt enhancing properties of the compounds of the present invention are important because it allows flavorists to provide the desired salty taste profile in foods and beverages without actually having higher salt levels in the food. Therefore the consumer can have both the taste profile that they desire while without having the adverse health effects associated with increased salt levels such as hypertension.

As used herein olfactory effective amount is understood to mean the amount of compound in flavor compositions the individual component will contribute to its particular olfactory characteristics, but the flavor, taste and aroma effect on the overall composition will be the sum of the effects of each of the flavor ingredients. As used herein taste effects include salt and umami, effects. Thus the compounds of the invention can be used to alter the taste characteristics of the flavor composition by modifying the taste reaction contributed by another ingredient in the composition. The amount will vary depending on many factors including other ingredients, their relative amounts and the effect that is desired.

The level of alkyldienamides used in products is greater than 50 parts per billion, generally provided at a level of from about 50 parts per billion to about 800 parts per million in the finished product, more preferably from about 10 parts per million to about 500 parts per million by weight.

The usage level of alkyldienamides varies depending on the product in which the alkyldienamides are employed. For examples, alcoholic beverages the usage level is from about 1 to about 50 parts per million, preferably from about 5 to about 30 and most preferably from about 10 to about 25 parts per million by weight. Non-alcoholic beverages are flavored at levels of from about 50 parts per billion to about 5 parts per million, preferably from about 200 parts per billion to about 1 part per million and in highly preferred situations of from about 300 to about 800 parts per billion. Snack foods can be advantageously flavored using alkyldienamides of the present invention at levels of from about 10 to about 250 parts per million, preferably from about 50 to about 200 and most preferably from about 75 to about 150 parts per million by weight.

Toothpaste can be satisfactorily flavored by using alkyldienamides at levels of from about 150 to about 500 parts per million, more preferably from about 200 to about 400 parts per million by weight.

Candy products including hard candy can be flavored at levels of from about 10 to about 200; preferably from about 25 to about 150 and more preferably from 50 to 100 parts per million by weight. Gum usage levels are from about 300 to about 800, preferably from about 450 to about 600 parts per million.

The present invention also provides a method for enhancing or modifying the salt flavor of a food through the incorporation of an organoleptically acceptable level of the compounds described herein. The compounds can be used individually or in combination with other salt enhancing compounds of the present invention. In addition, the salt enhancing materials of the present invention can be used in combination with other salt enhancing compositions known in the art, including but not limited to cetylpyridium chloride, bretylium tosylate, various polypeptides, mixtures of calcium salts of ascorbic acid, sodium chloride and potassium chloride, as described in various U.S. Pat. Nos. 4,997,672; 5,288,510; 6,541,050 and 6,974,597.

The salt taste enhancing compounds of the present invention may be employed to enhance the perceived salt taste of any salts used in food or beverage products. The preferred salt taste to be enhanced by the compounds of the present invention is that of sodium chloride, primarily because of the discovery that ingestion of large amounts of sodium may have adverse effects on humans and the resultant desirability of reducing salt content while retaining salt taste.

In addition, the compounds of the present invention may also be employed to enhance the perceived salt taste of known salty tasting compounds which may be used as salt substitutes. Such compounds include cationic amino acids and low molecular weight dipeptides. Specific examples of these compounds are arginine, hydrochloride, lysine hydrochloride and lysine-ornithine hydrochloride. These compounds exhibit a salty taste but are typically useful only at low concentrations since they exhibit a bitter flavor at higher concentrations. Thus, it is feasible to reduce the sodium chloride content of a food or beverage product by first formulating a food or beverage with less sodium chloride than is necessary to achieve a desired salt taste and then adding to said food or beverage the compounds of the present invention in an amount sufficient to potentiate the salt taste of said salted food or beverage to reach said desired taste. In addition, the sodium chloride content may be further reduced by substituting a salty-tasting cationic amino acid, a low molecular weight dipeptide or mixtures thereof for at least a portion of the salt.

The salt enhancing level of the compounds of the present invention range from about 100 parts per billion to about 100 parts per million; preferably from about 0.1 parts per million to about 50 parts per million; and most preferably from about 0.5 parts per million to about 10 parts per million when incorporated into the foodstuff.

The term "foodstuff" as used herein includes both solid and liquid ingestible materials for man or animals, which materials usually do, but need not, have nutritional value. Thus, foodstuffs include food products, such as, meats, gravies, soups, convenience foods, malt, alcoholic and other beverages, milk and dairy products, seafood, including fish, crustaceans, mollusks and the like, candies, vegetables, cereals, soft drinks, snacks, dog and cat foods, other veterinary products and the like.

When the alkyldienamides compounds of this invention are used in a flavoring composition, they can be combined with conventional flavoring materials or adjuvants. Such co-ingredients or flavor adjuvants are well known in the art for such use and have been extensively described in the literature. Requirements of such adjuvant materials are: (1) that they be non-reactive with the alkyldienamides of our invention; (2) that they be organoleptically compatible with the alkyldienamides derivative(s) of our invention whereby the flavor of the ultimate consumable material to which the alkyldienamides are added is not detrimentally affected by the use of the adjuvant; and (3) that they be ingestible acceptable and thus nontoxic or otherwise non-deleterious. Apart from these requirements, conventional materials can be used and broadly include other flavor materials, vehicles, stabilizers, thickeners, surface active agents, conditioners and flavor intensifiers.

Such conventional flavoring materials include saturated fatty acids, unsaturated fatty acids and amino acids; alcohols including primary and secondary alcohols, esters, carbonyl compounds including ketones, other than the alkyldienamides of our invention and aldehydes; lactones; other cyclic organic materials including benzene derivatives, acyclic compounds, heterocyclics such as furans, pyridines, pyrazines and the like; sulfur-containing compounds including thiols, sulfides, disulfides and the like; proteins; lipids, carbohydrates; so-called flavor potentiators such as monosodium glutamate; magnesium glutamate, calcium glutamate, guanylates and inosinates; natural flavoring materials such as hydrolyzates, cocoa, vanilla and caramel; essential oils and extracts such as anise oil, clove oil and the like and artificial flavoring materials such as vanillin, ethyl vanillin and the like.

Specific preferred flavor adjuvants include but are not limited to the following: anise oil; ethyl-2-methyl butyrate; vanillin; cis-3-heptenol; cis-3-hexenol; trans-2-heptenal; butyl valerate; 2,3-diethyl pyrazine; methyl cyclo-pentenolone; benzaldehyde; valerian oil; 3,4-dimethoxy-phenol; amyl acetate; amyl cinnamate; γ-butyryl lactone; furfural; trimethylpyrazine; phenyl acetic acid; isovaleraldehyde; ethyl maltol; ethyl vanillin; ethyl valerate; ethyl butyrate; cocoa extract; coffee extract; peppermint oil; spearmint oil; clove oil; anethol; cardamom oil; wintergreen oil; cinnamic aldehyde; ethyl-2-methyl valerate; γ-hexenyl lactone; 2,4-decadienal; 2,4-heptadienal; methyl thiazole alcohol (4-methyl-5-β-hydroxyethyl thiazole); 2-methyl butanethiol; 4-mercapto-2-butanone; 3-mercapto-2-pentanone; 1-mercapto-2- propane; benzaldehyde; furfural; furfuryl alcohol; 2-mercapto propionic acid; alkyl pyrazine; methyl pyrazine; 2-ethyl-3-methylpyrazine; tetramethylpyrazine; polysulfides; dipropyl disulfide; methyl benzyl disulfide; alkyl thiophene; 2,3-dimethyl thiophene; 5-methyl furfural; acetyl furan; 2,4-decadienal; guiacol; phenyl acetaldehyde; β-decalactone; d-limonene; acetoin; amyl acetate; maltol; ethyl butyrate; levulinic acid; piperonal; ethyl acetate; n-octanal; n-pentanal; n-hexanal; diacetyl; monosodium glutamate; monopotassium glutamate; sulfur-containing amino acids, e.g., cysteine; hydrolyzed vegetable protein; 2-methylfuran-3-thiol; 2-methyldihydrofuran-3-thiol; 2,5-dimethylfuran-3-thiol; hydrolyzed fish protein; tetramethylpyrazine; propylpropenyl disulfide; propylpropenyl trisulfide; diallyl disulfide; diallyl trisulfide; dipropenyl disulfide; dipropenyl trisulfide; 4-methyl-2-[(methylthio)-ethyl]-1,3-dithiolane; 4,5-dimethyl-2-(methylthiomethyl)-1,3-dithiolane; and 4-methyl-2-(methylthiomethyl)-1,3-dithiolane. These and other flavor ingredients are provided in U.S. Pat. Nos. 6,110,520 and 6,333,180 hereby incorporated by reference.

The alkyldienamides derivative(s) of our invention or compositions incorporating them, as mentioned above, can be combined with one or more vehicles or carriers for adding them to the particular product. Vehicles can be edible or otherwise suitable materials such as ethyl alcohol, propylene glycol, water and the like, as described supra. Carriers include materials such as gum arabic, carrageenan, xanthan gum, guar gum and the like.

Alkyldienamides prepared according to our invention can be incorporated with the carriers by conventional means such as spray-drying, extrusion, drum-drying and the like. Such carriers can also include materials for coacervating the alkyldienamides of our invention to provide encapsulated products, as set forth supra. When the carrier is an emulsion, the flavoring composition can also contain emulsifiers such as mono- and diglycerides or fatty acids and the like. With these carriers or vehicles, the desired physical form of the compositions can be prepared.

The quantity of alkyldienamides utilized should be sufficient to impart the desired flavor characteristic to the product, but on the other hand, the use of an excessive amount of alkyldienamides is not only wasteful and uneconomical, but in some instances, too large a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage, if any, to which the product will be subjected; and the preconsumption treatment such as baking, frying and so on, given to the product by the ultimate consumer. Accordingly, the terminology "effective amount" and "sufficient amount" is understood in the context of the present invention to be quantitatively adequate to alter the flavor of the foodstuff.

With reference to the novel compounds of our invention, the synthesis is effected by means of the reaction of Z4-aldehydes with malonic acid under pyridine catalysis to furnish the known E2,Z6-acids. Subsequent reaction with ethyl chloroformate in the presence of triethylamine and further reaction of the intermediate with amine (added either directly or in solution) according to the general scheme:

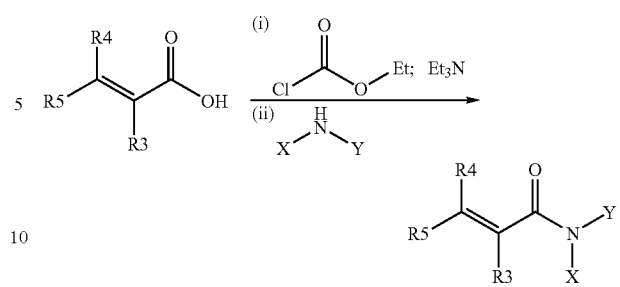

More specifically, with reference to the novel compounds of our invention, the synthesis is effected by means of the reaction of Z4-aldehyde with malonic acid under pyridine catalysis to furnish the known E2,Z6-acids. Subsequent reaction with ethyl chloroformate in the presence of triethylamine and further reaction of the intermediate with amine (added either directly or in solution) according to the scheme:

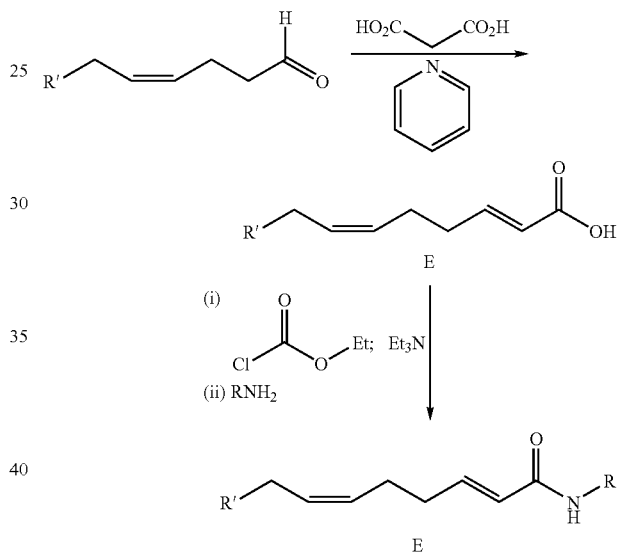

as set forth in examples herein. The acid is dissolved in dichloromethane to which ethylchloroformate is added in 1.0 to 2.0 equivalents at temperatures ranging from 0° C. to room temperature, most preferably from 10° C. to 20° C. The resulting solution is cooled to −10° C. to −30° C., and triethylamine is added in 1.0 to 2.0 equivalents such that the temperature range is below 0° C. and the mixture aged for 1 hour.

The mixture is filtered, and the filtrate cooled to 0° C. The amine is added in 1.0 to 7.0 equivalents either neat or as a solution in THF and the reaction is aged for about 1-3 hours at room temperature.

The reaction can be quenched with aqueous sodium chloride, hydrogen chloride or sodium hydroxide depending of the need to remove residual acid or amine. The mixture is extracted into ethereal solvent or dichloromethane, washed to neutrality and solvent removed.

The crude product is purified by distillation or recrystallization depending on the physical properties.

The reaction occurs in 35-75% mole yield based on E2,Z6-acid.

The alkyldienamides of the present invention can be admixed with other flavoring agents and incorporated into foodstuffs and other products using techniques well known to those with ordinary skill in the art. Most commonly the alkyldienamides are simply admixed using the desired ingredients within the proportions stated.

The following are provided as specific embodiments of the present invention. Other modifications of this invention will be readily apparent to those skilled in the art, without departing from the scope of this invention. As used herein, both specification and following examples all percentages are weight percent unless noted to the contrary.

All U.S. patents cited herein are incorporated by reference as if set forth in their entirety.

Example 1

Preparation of Materials of the Present Invention

The following reaction sequence was used to prepare the specific compounds described by the NMR data set forth below:

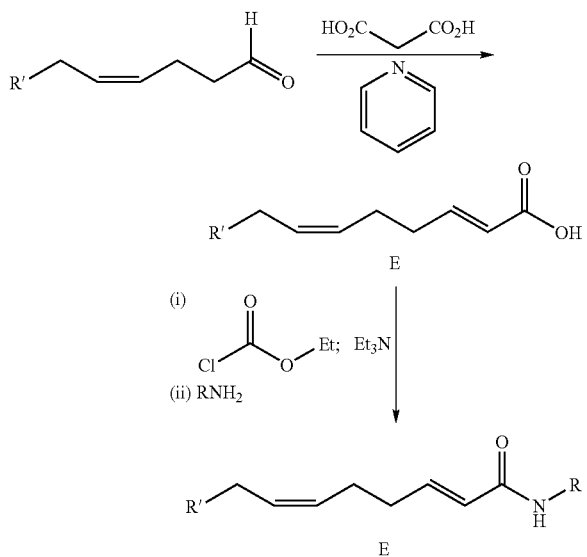

The acid is dissolved in dichloromethane to which ethylchloroformate is added in 1.0 to 2.0 equivalents at temperatures ranging from 0° C. to room temperature, most preferably from 10° C. to 20° C. The resulting solution is cooled to −10° C. to −30° C., and triethylamine is added in 1.0 to 2.0 equivalents such that the temperature range is below 0° C. and the mixture aged for 1 hour.

The mixture is filtered, and the filtrate cooled to 0° C. The amine is added in 1.0 to 7.0 equivalents either neat or as a solution in THF and the reaction is aged for 1-3 hours at room temperature.

The reaction can be quenched with aqueous sodium chloride, hydrogen chloride or sodium hydroxide depending on the need to remove residual acid or amine. The mixture is extracted into ethereal solvent or dichloromethane, washed to neutrality and solvent removed.

The crude product is purified by distillation or recrystallization depending on the physical properties.

The amides are synthesized according to the general scheme above with the following specific examples. Equivalents set out are mole equivalents based on starting acid, yields are distilled chemical yields based on starting acid.

N-methyl 2E,6Z-nonadienamide 2E,6Z-nonadienoic acid 1 eq, ethyl chloroformate 1.5 eq, triethylamine 1.5 eq, methylamine 1.5 eq as a 2.0M solution in THF, quench with 10% sodium chloride solution, yield=47%.
0.95 ppm (t, 3H, J=7.54 Hz, a), 2.02 ppm (quintet, 2H, J=7.33 Hz),
2.19 ppm (m, 4H, c), 2.78 & 2.85 ppm (d, 3H, J=4.81 & 4.87 Hz),
5.27-5.43 ppm (m, 2H, e), 5.90 ppm (d, 1H, J=15.36 Hz),
6.80 ppm (d, 1H, J=15.33 Hz, of t, J=6.59 Hz, g), 6.80 ppm (m, 1H).

N-ethyl 2E,6Z-nonadienamide 2E,6Z-nonadienoic acid 1 eq, ethyl chloroformate 1.5 eq, triethylamine 1.5 eq, ethylamine 7.0 eq as a 2.0M solution in THF, quench with 10% hydrogen chloride solution, yield=60%.
0.95 ppm (t, 3H, J=7.55 Hz), 1.16 ppm (t, 3H, J=7.27 Hz),
2.03 ppm (quintet, 2H, J=7.31 Hz), 2.20 ppm (m, 4H),
3.35 ppm (quintet, 2H, J=7.04 Hz), 5.27-5.44 ppm (m, 2H),
5.84 ppm (d, 1H, J=15.32 Hz), 6.16 ppm (br. s, 1H),
6.82 ppm (d, 1H, J=15.28 Hz, of t, J=6.51 Hz).

N-ethyl 2E,6Z-dodecadienamide 2E,6Z-dodecadienoic acid 1 eq, ethyl chloroformate 1.5 eq, triethylamine 1.5 eq, ethylamine 7.0 eq as a 2.0M solution in THF, quench with 10% hydrogen chloride solution, yield=65%.
0.89 ppm (t, 3H, J=6.86 Hz), 1.16 ppm (t, 3H, J=7.27 Hz),
1.29 ppm (m, 6H), 2.01 ppm (q, 2H, J=6.79 Hz),
2.20 ppm (m, 4H), 3.35 ppm (m, 2H),
5.30-5.44 ppm (m, 2H), 5.80 ppm (d, 1H, J=15.32 Hz),
5.87 ppm (br. s, 1H), 6.82 ppm (d, 1H, J=15.29 Hz, J=6.61 Hz).

N-isopropyl 2E,6Z-nonadienamide 2E,6Z-nonadienoic acid 1 eq, ethyl chloroformate 1.5 eq, triethylamine 1.5 eq, isopropylamine 3.0 eq, quench with 20% sodium chloride, yield=57%.
0.95 ppm (t, 3H, J=7.53 Hz), 1.17 ppm (d, 6H, J=6.59 Hz),
2.03 ppm (quintet, 2H, J=7.36 Hz), 2.19 ppm (m, 4H), 4.14 ppm (m, 1H), 5.27-5.44 ppm (m, 2H),
5.83 ppm (d, 1H, J=15.30 Hz), 5.99 ppm (br. s, 1H),
6.81 ppm (d, 1H, J=15.27 Hz, J=6.64 Hz).

N-isopropyl 2E,6Z-dodecadienamide 2E,6Z-dodecadienoic acid 1 eq, ethyl chloroformate 1.5 eq, triethylamine 1.5 eq, isopropylamine 3.0 eq, quench with 20% sodium chloride, yield=52%.
0.88 ppm (t, 3H, J=7.53 Hz), 1.18 ppm (d, 6H, J=6.59 Hz), 1.29 ppm (m, 6H),
2.02 ppm (q, 2H, J=7.36 Hz), 2.20 ppm (m, 4H), 4.14 ppm (m, 1H), 5.27-5.44 ppm (m, 2H), 5.62 ppm (br. s, 1H), 5.78 ppm (d, 1H, J=15.30 Hz),
6.79 ppm (d, 1H, J=15.27 Hz, of t, J=6.64 Hz).

N-isobutyl 2E,6Z-nonadienamide 2E,6Z-nonadienoic acid 1 eq, ethyl chloroformate 1.2 eq, triethylamine 1.5 eq, isobutylamine 1.0 eq, quench with 10% sodium hydroxide, yield=33%.

0.92 ppm (d, 6H, J=6.74 Hz), 0.95 ppm (t, 3H, J=7.51 Hz), 1.80 ppm (septet, 1H, J=6.73 Hz), 2.03 ppm (quintet, 2H, J=7.27 Hz), 2.20 ppm (m, 4H), 3.14 ppm (t, 2H, J=6.53 Hz), 5.28-5.47 ppm (m, 2H), 5.85 ppm (d, 1H, J=15.29 Hz), 5.88 ppm (br. s, 1H), 6.82 ppm (d, 1H, J=15.27 Hz, of t, J=6.61 Hz).

N-isobutyl 2E,6Z-dodecadienamide 2E,6Z-dodecadienoic acid 1 eq, ethyl chloroformate 1.2 eq, triethylamine 1.5 eq, isobutylamine 3.0 eq, quench with 10% hydrogen chloride solution, yield=41%.

0.88 ppm (t, 3H, J=6.99 Hz), 0.92 ppm (d, 6H, J=6.70 Hz), 1.29 ppm (m, 6H), 1.80 ppm (m, 1H, J=6.73 Hz), 2.01 ppm (q, 2H, J=6.75 Hz), 2.20 ppm (m, 4H), 3.14 ppm (t, 2H, J=6.47 Hz), 5.30-5.44 ppm (m, 2H), 5.84 ppm (d, 1H, J=15.30 Hz), 5.97 ppm (m, 1H), 6.82 ppm (d, 1H, J=15.28 Hz, of t, J=6.55 Hz).

N-(2-methylbutyl) 2E,6Z-nonadienamide 2E,6Z-nonadienoic acid 1 eq, ethyl chloroformate 1.5 eq, triethylamine 1.5 eq, 2-methylbutylamine 3.0 eq, quench with 20% sodium chloride, yield=37%.

0.90 ppm (d, 3H, J=6.57 Hz), 0.90 ppm (t, 3H, J=7.45 Hz), 0.96 ppm (t, 3H, J=7.55 Hz), 1.17 ppm (m, 1H), 1.42 ppm (m, 1H), 1.58 ppm (m, 1H), 2.03 ppm (quintet, 2H, J=7.33 Hz), 2.20 ppm (m, 4H), 3.09-3.29 ppm (m, 2H), 5.28-5.44 ppm (m, 2H), 5.80 ppm (br. s, 1H), 5.82 ppm (d, 1H, J=15.34 Hz), 6.82 ppm (d, 1H, J=15.23 Hz, of t, J=6.55 Hz).

N-(2-methylbutyl) 2E,6Z-dodecadienamide 2E,6Z-dodecadienoic acid 1 eq, ethyl chloroformate 1.5 eq, triethylamine 1.5 eq, 2-methylbutylamine 3.0 eq, quench with 20% sodium chloride, yield=45%.

0.7-0.92 ppm (m, 9H), 1.17 ppm (m, 1H), 1.29 ppm (m, 6H), 1.36 ppm (m, 1H), 1.57 ppm (m, 1H), 2.01 ppm (q, 2H, J=6.82 Hz), 2.20 ppm (m, 4H), 3.09-3.29 ppm (m, 2H), 5.30-5.44 ppm (m, 2H), 5.82 ppm (br. s, 1H), 5.83 ppm (d, 1H, J=15.27 Hz), 6.82 ppm (d, 1H, J=15.26 Hz, of t, J=6.58 Hz).

N-cyclopropyl 2E,6Z-nonadienamide 2E,6Z-nonadienoic acid 1 eq, ethyl chloroformate 1.5 eq, triethylamine 1.5 eq, cyclopropylamine 2.0 eq, quench with 10% hydrogen chloride solution, yield=49%.

0.53 ppm (m, 2H), 0.77 ppm (m, 2H), 0.95 ppm (t, 3H, J=7.53 Hz), 2.02 ppm (quintet, 2H, J=7.37 Hz), 2.19 ppm (m, 4H), 2.77 ppm (m, 1H), 5.26-5.43 ppm (m, 2H), 5.79 ppm (d, 1H, J=15.30 Hz), 6.15 ppm (br. s, 1H), 6.82 ppm (d, 1H, J=15.30 Hz, of t, J=6.58 Hz).

N-cyclopropyl 2E,6Z-dodecadienamide 2E,6Z-dodecadienoic acid 1 eq, ethyl chloroformate 1.5 eq, triethylamine 1.5 eq, cyclopropylamine 2.4 eq, quench with 10% hydrogen chloride solution, yield=55%.

0.53 ppm (m, 2H), 0.76 ppm (m, 2H), 0.88 ppm (t, 3H, J=6.85 Hz), 1.29 ppm (m, 6H), 2.00 ppm (q, 2H, J=6.80 Hz), 2.18 ppm (m, 4H), 2.78 ppm (m, 1H), 5.29-5.43 ppm (m, 2H), 5.83 ppm (d, 1H, J=15.34 Hz), 6.46 ppm (br. s, 1H), 6.82 ppm (d, 1H, J=15.30 Hz, of t, J=6.52 Hz).

N-(2-hydroxyethyl) 2E,6Z-dodecadienamide 2E,6Z-dodecadienoic acid 1 eq, ethyl chloroformate 1.5 eq, triethylamine 1.5 eq, 2-ethanolamine 3.0 eq, quench with 20% sodium chloride and washed with dilute hydrogen chloride solution, yield=48%.

0.89 ppm (t, 3H, J=7.05 Hz), 1.29 ppm (m, 6H), 2.01 ppm (q, 2H, J=7.01 Hz), 2.20 ppm (m, 4H), 3.47 ppm (m, 2H), 3.73 ppm (m, 2H), 4.17-4.28 ppm (br. m, 1H), 5.29-5.44 ppm (m, 2H), 5.84 ppm (d, 1H, J=15.37 Hz), 6.43-6.47 ppm (br. m, 1H), 6.84 ppm (d, 1H, J=15.31 Hz, of t, J=6.54 Hz).

N-(3,4-methylenedioxy)benzyl 2E,6Z-nonadienamide 2E,6Z-nonadienoic acid 1 eq, ethyl chloroformate 1.5 eq, triethylamine 1.5 eq, piperonylamine 1.5 eq, quench with 10% sodium hydroxide solution, re-crystallized from hexane, yield=72%.

0.95 ppm (t, 3H, J=7.53 Hz), 2.03 ppm (quintet, 2H, J=7.37 Hz), 2.20 ppm (m, 4H), 4.39 ppm (d, 2H, J=5.76 Hz), 5.27-5.44 ppm (m, 2H), 5.76 ppm (br. s, 1H), 5.78 ppm (d, 1H, J=15.38 Hz), 5.94 ppm (s, 2H), 6.75-6.79 ppm (m, 3H), 6.86 ppm (d, 1H, J=15.27 Hz, of t, J=6.59 Hz).

N-ethyl 3-(3-cyclohexenyl)-2E-propenamide 3-(3-Cyclohexenyl)-2E-propenoic acid 1 eq, ethyl chloroformate 1.5 eq, triethylamine 1.5 eq, ethylamine 1.5 eq as a 2.0M solution in THF, quench with 10% sodium chloride solution, yield=39%.

1.17 ppm (t, 3H, J=7.25 Hz), 1.45 ppm (m, 1H), 1.80-1.83 ppm (m, 1H), 1.88-1.94 ppm (m, 1H), 2.09 ppm (m, 3H), 2.41 ppm (br. s, 1H), 3.36 ppm (m, 2H), 5.68 ppm (br. s, 3H), 5.77 ppm (d, 1H, J=15.40 Hz), 6.83 ppm (d, 1H, J=15.39 Hz, of d, J=7.02 Hz)

N-cyclopropyl 3-(3-cyclohexenyl)-2E-propenamide 3-(3-Cyclohexenyl)-2E-propenoic acid 1 eq, ethyl chloroformate 1.5 eq, triethylamine 1.5 eq, cyclopropylamine 1.6 eq, quench with 10% sodium chloride solution, yield=69%.

0.53 ppm (d, 2H, J=1.96 Hz), 0.79 ppm (d, 2H, J=5.59 Hz), 1.44 ppm (m, 1H), 1.82 ppm (m, 1H), 1.93 ppm (m, 1H), 2.08 ppm (m, 3H), 2.40 ppm (br. s, 1H), 2.78 ppm (m, 1H), 5.68 ppm (s, 2H), 5.73 ppm (d, 1H, J=15.58 Hz), 5.82 ppm (br. s, 1H), 6.84 ppm (d, 1H, J=15.41 Hz, of d, J=7.02 Hz)

N-allyl 2E,6Z-nonadienamide 2E,6Z-Nonadienoic acid 1 eq, ethyl chloroformate 1.5 eq, triethylamine 1.5 eq, allylamine 1.5 eq, quench with 10% sodium chloride solution, yield=58%.

0.95 ppm (t, 3H, J=7.560 Hz), 2.03 ppm (quintet, 2H, J=7.37 Hz), 2.18-2.23 ppm (m, 4H), 3.93 ppm (t, 2H, J=5.59 Hz), 5.16 ppm (d, 2H, J=17.14 Hz, of, J=10.23 Hz), 5.30-5.43 ppm (m, 2H), 5.83-5.89 ppm (m, 1H), 5.86 ppm (d, 1H, J=14.02 Hz), 6.10 ppm (br. s, 1H), 6.81-6.86 ppm (d, 1H, J=15.29 Hz, of t, J=6.52 Hz)

N-allyl 3-methyl-2E-butenamide

3-Methyl-2E-butenoic acid 1 eq, ethyl chloroformate 1.5 eq, triethylamine 1.5 eq, allylamine 1.5 eq, quench with 10% sodium chloride solution, yield=46%.

1.83 ppm (s, 3H), 2.16 ppm (s, 3H), 3.90 ppm (t, 2H, J=5.63 Hz, of d, J=1.43 Hz), 5.11 ppm (t, 1H, J=10.22 Hz, of d, J=1.35 Hz), 5.18 ppm (t, 1H, J=17.15 Hz, of d, J=1.48 Hz), 5.62 ppm (s, 1H), 5.81-5.89 ppm (m, 1H), 5.96 ppm (br. s, 1H)

N,N,3,7-tetramethyl-2E,6-octadienamide 3,7-Dimethyl-2E,6-octadienoic acid 1 eq, ethyl chloroformate 1.5 eq, triethylamine 1.5 eq, dimethylamine 1.5 eq as a 40 wt % solution in water, quench with 10% sodium chloride solution, yield=46%.

1.61 ppm (s, 3H), 1.68 ppm (s, 3H), 1.86 ppm (2s, 3H), 2.13-2.16 ppm (m, 3H), 2.34 ppm (t, 1H, J=7.76 Hz), 2.96-3.01 ppm (m, 6H), 5.11 ppm (m, 1H), 5.78 ppm (m, 1H)

N-(carbomethoxy)methyl 2E,6Z-nonadienamide 2E,6Z-Nonadienoic acid 1 eq, ethyl chloroformate 1.5 eq, triethylamine 1.5 eq, glycine 1.5 eq, quench with 10% sodium chloride solution, yield=62%.

0.96 ppm (t, 3H, J=7.53 Hz), 2.03 ppm (quintet, 2H, J=7.45 Hz), 2.19 ppm (t, 2H, J=6.44 Hz), 2.23 ppm (t, 2H, J=6.28 Hz), 3.75 ppm (s, 3H), 4.10 ppm (d, 2H, J=5.41 Hz), 5.31 ppm (m, 1H), 5.39 ppm (m, 1H), 5.91 ppm (d, 1H, J=15.37 Hz), 6.60 ppm (br. s, 1H), ppm (d, 1H, J=15.33 Hz, of t, J=6.57 Hz)

N-ethyl 4-(2,2,3-trimethyl-3-penten-1-yl)-2E-butenamide 4-(2,2,3-Trimethyl-3-penten-1-yl)-2E-butenoic acid 1 eq, ethyl chloroformate 1.5 eq, triethylamine 1.5 eq, ethylamine 1.5 eq as a 2.0M solution in THF, quench with 10% sodium chloride solution, yield=22%.

0.79 ppm (s, 3H), 0.99 ppm (s, 3H), 1.17 ppm (t, 3H, J=7.27 Hz), 1.60 ppm (s, 3H), 1.81-1.92 ppm (m, 2H), 2.07-2.13 ppm (m, 1H), 2.27-2.35 ppm (m, 2H), 3.36 ppm (q, 2H, J=7.22 Hz, of d, J=7.79 Hz), 5.22 ppm (s, 1H), 5.37 ppm (br. s, 1H), 5.77 ppm (d, 1H, J=15.20 Hz), 6.83 ppm (d, 1H, J=15.19 Hz, of t, J=7.31 Hz)

N-cyclopropyl 4-(2,2,3-trimethyl-3-penten-1-yl)-2E-butenamide 4-(2,2,3-Trimethyl-3-penten-1-yl)-2E-butenoic acid 1 eq, ethyl chloroformate 1.5 eq, triethylamine 1.5 eq, cyclopropylamine 1.5 eq, quench with 10% sodium chloride solution, yield=40%.

0.53 ppm (m, 90% of 2H), 0.62 ppm (m, 10% of 2H), 0.79 ppm (s, 3H), 0.80 ppm (m, 2H), 0.99 ppm (s, 3H), 1.60 ppm (s, 3H), 1.80-1.91 ppm (m 2H), 2.06-2.12 ppm (m, 1H), 2.30 ppm (m, 2H), 2.78 ppm (m, 1H), 5.21 ppm (s, 1H), 5.58 ppm (br. s, 1H), 5.74 ppm (d, 1H, J=15.20 Hz), 6.84 ppm (d, 1H, J=15.20 Hz, of t, J=7.31 Hz)

N,N-dimethyl 2E,6Z-Nonadienamide 2E,6Z-Nonadienoic acid 1 eq, ethyl chloroformate 1.5 eq, triethylamine 1.5 eq, dimethylamine 1.5 eq as a 40 wt % solution in water, quench with 10% sodium chloride solution, yield=63%.

0.96 ppm (t, 3H, J=7.53 Hz), 2.04 ppm (quintet, 2H, J=7.41 Hz), 2.18-2.28 ppm (m, 4H), 2.99 ppm (s, 3H), 3.07 ppm (s, 3H), 5.29-5.43 ppm (m, 2H), 6.26 ppm (d, 1H, J=15.10 Hz), 6.82-6.88 (d, 1H, 15.09 Hz, of d, J=6.72 Hz)

N-ethyl 5-phenyl-2E-pentenamide

5-Phenyl-2E-pentenoic acid 1 eq, ethyl chloroformate 1.5 eq, triethylamine 1.5 eq, ethylamine 1.5 eq as a 2.0M solution in THF, quench with 10% sodium chloride solution, yield=39%.

1.15 ppm (t, 3H, J=7.27 Hz), 2.49 ppm (m, 2H), 2.75 ppm (t, 2H, J=7.80 Hz), 3.34 ppm (q, 2H, J=7.24 Hz, of d, J=1.53 Hz), 5.60 ppm (br. s, 1H), 5.77 ppm (t, 1H, J=15.28 Hz, of t, J=1.52 Hz), 6.87 ppm (t, 1H, J=15.27 Hz, of t, J=6.87 Hz), 7.16-7.20 ppm (m, 3H), 7.26-7.29 ppm (m, 2H)

N-cyclopropyl 5-phenyl-2E-pentenamide

5-Phenyl-2E-pentenoic acid 1 eq, ethyl chloroformate 1.5 eq, triethylamine 1.5 eq, cyclopropylamine 1.5 eq, quench with 10% sodium chloride solution, yield=85%.

N-ethyl 2E,6Z-dodecadienamide 2E,6Z-dodecadienoic acid 1 eq, ethyl chloroformate 1.5 eq, triethylamine 1.5 eq, methylamine 5.0 eq as a 2.0M solution in THF, quench with 10% hydrogen chloride solution, yield=59%.

N-ethyl 3,7-dimethyl-2E,6-octadienamide 3,7-Dimethyl-2E,6-octadienoic acid 1 eq, ethyl chloroformate 1.5 eq, triethylamine 1.5 eq, ethylamine 3.05 eq as a 70 wt % solution in water, quench with 10% sodium chloride solution, yield=51%.

N,N-Diisopropyl-3-methyl-2E-hexenamide

3-Methyl-2E-hexenoic acid 1 eq, ethyl chloroformate 1.5 eq, triethylamine 1.6 eq, diisopropylamine 3.0 eq, quench with 10% hydrogen chloride solution, yield=34%.

Example 2

Preparation of Non-Alcoholic Beverage Flavor System

A non-alcoholic beverage formulation was prepared according to the following formulation.

| | |
|---|---|
| Water | 866.82 grams |
| High Fructose Corn Syrup 55 (77° Brix) | 129.8 grams |
| Citric Acid | 3.38 grams |

The flavor applied to the beverages consisted of a blend of single fold lemon oil and distilled lime oil. The control beverage contained 35 PPM of this flavor. This control beverage exhibited the taste characteristics of a tart lemon lime flavor. Another beverage was prepared containing 35 PPM of the same flavor and 0.5 PPM of N-Ethyl E2,Z6-nonadienamide. This beverage exhibited enhanced flavor impact, increased tartness, and an increased perception of freshness as well as it being described as having a more "natural" flavor.

Example 3

Preparation of an Alcoholic Beverage Flavor System

Flavored beverages were prepared using the following 30° Proof alcoholic base:

| | |
|---|---|
| 190° Proof food grade Ethyl Alcohol | 157.89 milliliters |
| High Fructose Corn Syrup 55 (77° Brix) | 217.00 milliliters |
| Citric Acid (50% solution) | 3.00 milliliters |
| Water | 622.11 milliliters |

The peach flavor applied to the beverages consisted of a blend of Gamma Decalactone, Benzaldehyde, Cis-3-hexenol, Butyric acid, 2-Methyl butyric acid, Iso butyl acetate, Linalool, and para-Mentha-8-thiol-3-one. The control beverage contained 60 PPM of the above flavor blend. This control beverage exhibited the taste characteristics of a mild candied green peach. Another beverage was prepared containing 60 PPM of the same flavor and 20 PPM of N-(3,4-methylenedioxy) benzyl E2,Z6-nonadienamide. This beverage exhibited an enhanced perception of alcohol, increased flavor impact, and a tingle effect on the tongue.

Example 4

Preparation of a Toothpaste Product

The following separate groups of ingredients were prepared:

Group "A"

| Ingredients | weight Percent |
|---|---|
| glycerin | 30.2 |
| distilled water | 15.3 |
| sodium benzoate | 0.1 |
| sodium saccharin | 0.2 |
| stannous flouride | 0.5 |

Group "B"

| Ingredients | Weight Percent |
|---|---|
| calcium carbonate | 12.5 |
| dicalcium phosphate (dihydrate) | 37.2 |

Group "C"
2.0 parts by weight of sodium n-Lauroyl sarcosinate (foaming agent)

Group "D"
1.0 parts by weight of the flavor material which is a blend of peppermint oil, spearmint oil, anethole, and menthol.

Procedure:
(1) The ingredients in Group "A" were stirred and heated in a steam jacketed kettle to 160° F.
(2) Stirring was continued for an additional 3 to 5 minutes to form a homogeneous gel.
(3) The powders of Group "B" were added to the gel, while mixing until a homogeneous paste is formed.
(4) With stirring, the flavor of Group "D" was added, followed by addition immediately thereafter of the foaming agent of Group "C".
(5) The resultant slurry was then blended for one hour.

The completed paste was then transferred to a three-roller mill, homogenized and finally tubed. The resulting toothpaste when used in a normal tooth brushing procedure yields a slightly bitter/medicinal mint flavor which exhibits moderate cooling. To this control paste 200 ppm of N-Isobutyl E2,Z6-dodecadienamide is added. This toothpaste exhibits moderate cooling without the bitterness of the control sample. In addition, the sample exhibited tingle on the tongue and a slight numbing on the lips.

Example 5

Preparation of a Chewing Gum Flavor 100 parts by weight of vehicle were mixed with 5 parts by weight of bubble gum flavor which is a blend of orange oil, amyl acetate, clove bud oil, ethyl butyrate, and methyl salicylate. To this 300 parts sucrose and 100 parts corn syrup were added. Mixing was effected in a ribbon blender with jacketed sidewalls of the type manufactured by Baker Perkins Co. The resultant chewing gum blend was then manufactured into strips 1 inch in width and 0.1 inches in thickness. These strips were cut into lengths of 3 inches each. This control gum exhibited a fruity citrus spice flavor when chewed. Another gum sample was prepared using the above recipe with the addition of 0.25 parts of N-Isobutyl E2,Z6-nonadienamide. The resulting gum had a similar taste profile to the control gum, however, it exhibited a pleasant tingle effect when chewed.

Example 6

Preparation of Flavor for Use in Hard Candy

| | |
|---|---|
| Sugar | 137 grams |
| Corn Syrup 42 DE | 91 grams |
| Water | 46 grams |

The above ingredients were added to a stainless steel pot. With constant mixing the ingredients were brought to 295° F. The pot was removed from the heat and 0.5 grams of cinnamon bark oil was blended in. This liquid candy was then deposited into molds where it was left to cool. This recipe yielded 200 grams of finished candy. The resulting control candy exhibited a cinnamon bark type flavor with low to moderate warmth. Another candy sample was prepared using the above recipe with the addition of 100 PPM of N-Methyl E2,Z6-nonadienamide. This candy exhibited a greener flavor with less warmth, a slight numbing and a moderate level of tingle.

Example 7

Use of the Compounds as Salt Enhancer

A trained consumer panel evaluated a series of molecules set forth below in a tasting solutions and were asked to rate the perception of the salty and umami character of each taste solution. The molecules employed in the test were:

2,6-Nonadienamide,N-2-Propenyl-,(2E,6Z)
2,6-Dodecadienamide,N-Ethyl-(2E,6Z)
N-Isobutyl-(E2,Z6)-Nonadienamide
(6Z,2E)-N-(2-Hydroxyethyl)dodeca-2,6-dienamide
(6Z,2E)-n-(methylethyl)nona-2,6-dienamide
2,6-Nonadienamide,N-ethyl-,(2E,6Z)
(2E)-N,N,3,7-Tetramethylocta-2,6-dienamide
2-Propenamide,3-(3-cyclohexen-1-yl)-N-ethyl-,(2E)
2,6-Dodecadienamide,N-cyclopropyl-,(2E,6Z)
(6Z,2E)-N-(methylethyl)dodeca-2,6-dienamide
n-Cyclopropyl-E2,Z6)-Nonadienamide
2-Propenamide,3-(2-cyclohexen-1-yl)-n-cyclopropyl-,(2E)

The taste solutions presented to the panelists contained 0.3% by weight NaCl, and varying amounts of monosodium glutamate and Ribotides (a commercially available blend of disodium guanylate and disodium inosinate). The MSG content of the taste solutions varied from 0 to 0.18% by weight and the Ribotides varied from 0% to 0.013% by weight. The molecules of this invention were added to the tasting solution in amounts varying between 0 to 1.3 parts per million by weight.

The taste panel found the molecules of the invention increased the perception of saltiness as much as 40% and a smaller but still significant increase in the umami perception of up to 17%.

The panel of flavorists and food technologists were asked to evaluate a series of reduced sodium chicken broth versus a full sodium chicken broth. In this degree of difference testing, the panel was able to find a significant difference in the taste of chicken broth containing 10% less salt. The panel found the difference in the taste of the low salt sample to be pronounced when the salt was reduced by 15%.

Samples of lower salt chicken broth containing 800 parts per billion of the molecules of the invention provided above were given to this panel for evaluation. The panel could not perceive the difference between the full salt chicken broth and the chicken broth with 15% less salt containing the molecules set forth above. A sample of broth containing molecules of this invention with a 20% reduction in salt was not perceived as significantly different from the full salt broth.

A commercially available rice side dish was prepared with and without the addition of molecules listed above. These molecules were added at 5 and 10 ppm to the prepared rice mix. The rice mix was then prepared on the stove top according to the directions on the package. A panel of flavorists and food technologists were asked to rate the saltiness or the samples. The panel found that the rice samples with the addition of the molecules were significantly saltier than the unflavored reference.

The molecules of this invention were added to a range of dairy products—yoghurt, sour cream, skim milk and full fat milk. The molecules were added in levels ranging from 1 to 5 ppm to the finished dairy product. A panel of flavorists and food technologists were presented the flavored and unflavored samples blind and asked to comment on the taste differences. The dairy samples containing the molecules were uniformly rated as creamier and more fatty tasting than the unflavored samples.

What is claimed is:

1. A compound having a structure:

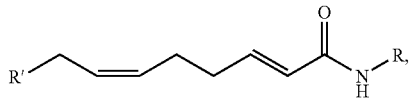

wherein R is ethyl or cyclopropyl; and
wherein R' is butyl.

2. A process for augmenting, enhancing, or imparting a taste or somatosensory effect to a foodstuff or a beverage, said process comprising the step of adding a taste or sensation augmenting, enhancing, or imparting level of a compound having a structure:

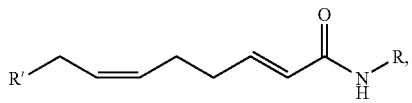

wherein R is ethyl or cyclopropyl; and
wherein R' is butyl.

3. The process of claim 2, wherein the level is greater than about 50 parts per billion by weight.

4. The process of claim 2, wherein the level is from about 100 parts per billion to about 100 parts per million by weight.

5. A foodstuff comprising the compound of claim 1.

6. A beverage comprising the compound of claim 1.

* * * * *